United States Patent
Lueken et al.

(10) Patent No.: US 8,129,571 B2
(45) Date of Patent: Mar. 6, 2012

(54) MULTISTAGE CONTINUOUS PROCESS FOR THE HYDROFORMYLATION OF HIGHER OLEFINS OR OLEFIN MIXTURES

(75) Inventors: Hans-Gerd Lueken, Marl (DE); Alfred Kaizik, Marl (DE); Stefan Drees, Duelmen (DE); Wilfried Bueschken, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 119 days.

(21) Appl. No.: 12/682,500

(22) PCT Filed: Oct. 28, 2008

(86) PCT No.: PCT/EP2008/064569
§ 371 (c)(1),
(2), (4) Date: Apr. 9, 2010

(87) PCT Pub. No.: WO2009/080395
PCT Pub. Date: Jul. 2, 2009

(65) Prior Publication Data
US 2010/0210880 A1 Aug. 19, 2010

(30) Foreign Application Priority Data
Dec. 20, 2007 (DE) .................. 10 2007 061 648

(51) Int. Cl.
*C07C 45/50* (2006.01)
*C07C 29/14* (2006.01)
(52) U.S. Cl. ........................... 568/451; 568/880
(58) Field of Classification Search .................. 568/451, 568/880
See application file for complete search history.

(56) References Cited

U.S. PATENT DOCUMENTS

| | | | |
|---|---|---|---|
| 6,015,928 A | 1/2000 | Gubisch et al. |
| 6,720,457 B2 | 4/2004 | Drees et al. |
| 6,723,884 B1 | 4/2004 | Grenacher et al. |
| 6,960,699 B2 | 11/2005 | Toetsch et al. |
| 7,179,947 B2 | 2/2007 | Lueken et al. |

FOREIGN PATENT DOCUMENTS

| DE | 199 39 491 | 2/2001 |
|---|---|---|
| DE | 102 41 266 | 3/2004 |

OTHER PUBLICATIONS

U.S. Appl. No. 12/738,111, filed Apr. 15, 2010, Lueken, et al.

*Primary Examiner* — Sikarl Witherspoon
(74) *Attorney, Agent, or Firm* — Oblon, Spivak, McClelland, Maier & Neustadt, L.L.P.

(57) ABSTRACT

The invention relates to a process for the continuous preparation of aldehydes and/or alcohols having at least 6 carbon atoms by multistage hydroformylation of olefins or olefin mixtures having at least 5 carbon atoms in the presence of unmodified cobalt complexes, in which at least two reactors are operated at different temperatures in the temperature range from 100 to 220° C. and pressures of from 100 to 400 bar, which is characterized in that
a) one reactor is operated at temperatures above 160° C. by the one-pot process with simultaneous catalyst formation, catalyst extraction and hydroformylation and the amount of water fed into the reactor with the aqueous cobalt salt solution is greater than that discharged from the reactor with the liquid reaction mixture and the gas phase together, with part of the aqueous bottom phase being discharged from the reactor to keep the level of the aqueous bottom phase constant,
b) and the cobalt carbonyls in the aqueous phase taken off or part thereof are introduced into the reactor which is operated at a lower temperature.

10 Claims, 2 Drawing Sheets

MULTISTAGE CONTINUOUS PROCESS FOR THE HYDROFORMYLATION OF HIGHER OLEFINS OR OLEFIN MIXTURES

The present invention relates to a process for the continuous preparation of aldehydes and/or alcohols by multistage hydroformylation of olefins or olefin mixtures in the presence of unmodified cobalt catalysts, in which part of the cobalt catalyst is transported from one reactor into another.

It is known that higher alcohols, in particular those having from 6 to 25 carbon atoms, can be prepared by catalytic hydroformylation (also known as the oxo process) of the olefins having one less carbon atom and subsequent hydrogenation of the aldehydes formed. The alcohols can be used as solvents or as precursors for detergents or plasticizers.

A large number of processes for the hydroformylation of olefins have been described in the literature. The choice of catalyst system and the optimal reaction conditions for the hydroformylation depend on the reactivity of the olefin used. The influence of the structure of the olefin used on its reactivity in a hydroformylation reaction is described, for example, by J. FALBE, "New Syntheses with Carbon Monoxide", Springer Verlag, 1980, Berlin, Heidelberg, New York, page 95 ff.

Industrial olefin mixtures which are used as starting materials for the hydroformylation reaction often contain olefin isomers having various structures and different degrees of branching, different positions of the double bond and olefins of different molar masses. This applies particularly to olefin mixtures which have been formed by dimerisation, trimerisation or further oligomerisation of olefins having from 2 to 8 carbon atoms or other readily available higher olefins or by cooligomerisation of the olefins mentioned. Examples of typical olefin mixtures which are of industrial relevance for hydroformylation are tripropene and tetrapropene and also dibutenes, tributenes and tetrabutenes.

In a hydroformylation carried out industrially, it is desirable to achieve not only a high conversion but also a high selectivity in order to ensure optimal utilization of the raw material. To achieve a high conversion, a relatively long reaction time and/or relatively high reaction temperatures often have to be accepted in the case of olefins which react slowly. More reactive olefins, on the other hand, can be converted into the aldehydes in a far shorter time under the same reaction conditions. In the joint hydroformylation of mixtures of olefins having differing reactivities, this leads to relatively long reaction times being required to achieve satisfactory conversion of the olefins which are more difficult to hydroformylate. However, the aldehydes formed from the more reactive olefins are formed relatively quickly and are then present together with the olefins which are more difficult to hydroformylate in the reactor. This leads to undesirable secondary and subsequent reactions of the aldehydes, e.g. to hydrogenation, to condensation reactions and to formation of acetals and hemiacetals. Owing to the differing reactivities of olefin isomers in particular, it is difficult to achieve high conversions and at the same time high selectivities in a hydroformylation reaction.

Apart from the unfavourable effect on the selectivity, there are two further aspects which stand in the way of joint hydroformylation of olefin mixtures in one step to high conversions. Firstly, the relatively long reaction times require relatively large reactor volumes at a given capacity or reactor output. This is a disadvantage particularly because hydroformylation processes are processes which occur under superatmospheric pressure and the capital costs of pressure reactors increase exponentially with size. Secondly, the desired product properties of the aldehydes, e.g. determined by the ratio of the linear (n) to branched (i) aldehydes (n/i ratio), are restricted in the control of the process.

As a solution to the differing reactivities, multistage processes, with or without intermediate removal of the products formed in a reaction stage, have been developed.

GB 1 387 657 describes a two-stage hydroformylation in which the reaction product of the first stage is discharged in gaseous form and after the aldehydes or alcohols have been condensed out, a part of the offgas of the first stage, which contains unreacted olefins, is recirculated to the first stage and the other part is fed to a second reactor.

A further variant of a two-stage hydroformylation is described in DE 32 32 557. In the first stage, the olefins are hydroformylated to conversions of from 50 to 90% using a cobalt catalyst, the cobalt catalyst is separated off from the reaction mixture and the aldehydes formed together with the unreacted olefins are introduced into a second hydroformylation stage. The ligand-modified cobalt catalyst used brings about not only the hydroformylation of the olefins but at the same time hydrogenation of the aldehydes to the alcohols.

DE 100 34 360 describes a process for the multistage cobalt- or rhodium-catalyzed hydroformylation of olefins having from 6 to 24 carbon atoms to alcohols and/or aldehydes, in which
a) the olefins are hydroformylated to a conversion of from 20 to 98% in a hydroformylation step,
b) the catalyst is removed from the liquid reactor output obtained in this way,
c) the liquid hydroformylation mixture obtained in this way is separated into a low boiling fraction containing olefins and paraffins and a bottom fraction containing aldehydes and/or alcohols,
d) the olefins present in the low boiling fraction are reacted in further process stages comprising the process steps a, b and c and the bottom fractions of the process steps c) of all process stages are combined.

This process is preferably carried out so that the liquid reactor output of the hydroformylation steps a) is a homogeneous liquid phase. The cobalt or rhodium catalysts are preferably used so that they are homogeneously dissolved in the liquid reactor output of the hydroformylation steps a).

EP 1 057 803 discloses a two-stage process for preparing alcohols from olefins or olefin mixtures. Here, the starting olefin is hydroformylated to an extent of from 50 to 90% in the presence of a cobalt catalyst in the first reaction stage. After the catalyst has been separated off, the unreacted olefins are separated off from the reaction product mixture by distillation and these olefins are reacted in the second hydroformylation reactor. The hydroformylation products from both stages can be hydrogenated to the corresponding alcohols. In both reaction stages, $CO_2(CO)_8$ or $HCo(CO)_4$ which is produced outside the hydroformylation reactors is used as catalyst. The cobalt catalyst is removed from the reaction mixture from the hydroformylation by extraction with a base before further processing.

Disadvantages of this process are the complicated catalyst work-up and the unsatisfactory yield. Thus, according to Example 5, a maximum yield of $C_9$ alcohol mixture of about 83% can be obtained from a butane dimer mixture.

A hydroformylation process in which the preparation of the active cobalt catalyst from an aqueous cobalt salt solution, extraction of the active cobalt catalyst into the organic phase and hydroformylation are carried out simultaneously in the same reactor is described, for example, in DE 196 54 340.

Since the catalytically active cobalt compounds (HCo$(CO)_4$ and $CO_2(CO)_8$) are formed only slowly from cobalt salts at temperatures below 160° C., an industrial process for the hydroformylation of olefins as described in DE 196 54 340 at temperatures below 160° C. is often not feasible.

However, higher temperatures in the hydroformylation promote the formation of by-products, for example the formation of paraffins by hydrogenation of starting olefins. For this reason, it can nevertheless be advantageous to operate at least one hydroformylation reactor at temperatures below 160° C. in a multistage hydroformylation process using unmodified cobalt catalysts in order to achieve a higher overall yield.

It was therefore an object of the invention to develop an improved process for preparing oxo aldehydes and/or alcohols by multistage hydroformylation of higher olefins using unmodified cobalt complexes as catalyst, in which smaller amounts of by-products are formed at least the same space-time yield.

It has now been found that in multistage continuous hydroformylation processes in which at least two reactors are operated at different temperatures using unmodified cobalt carbonyl catalysts, the space-time yield and/or selectivity can be increased if the amount of water introduced with the aqueous cobalt salt solution into the reactor in which the hydroformylation is carried out at temperatures above 160° C. by the one-pot process with simultaneous catalyst formation, extraction and hydroformylation is greater than that discharged with the liquid reaction product mixture and the synthesis gas together and the excess of water is removed by taking off part of the aqueous bottom phase and the cobalt carbonyls present therein are introduced into the reactor which is operated at a lower temperature.

The present invention accordingly provides a continuous process for preparing aldehydes and/or alcohols having at least 6 carbon atoms by multistage hydroformylation of olefins or olefin mixtures having at least 5 carbon atoms in the presence of unmodified cobalt complexes, in which at least two reactors are operated at different temperatures in the temperature range from 100 to 220° C. and pressures of from 100 to 400 bar, which is characterized in that a) one reactor is operated at temperatures above 160° C. by the one-pot process with simultaneous catalyst formation, catalyst extraction and hydroformylation and the amount of water fed into the reactor with the aqueous cobalt salt solution is greater than that discharged from the reactor with the liquid reaction mixture and the gas phase together, with part of the aqueous bottom phase being continuously discharged from the reactor to keep the level of the aqueous cobalt-containing bottom phase constant, b) and the cobalt carbonyls in the aqueous phase taken off or part thereof are introduced into the reactor which is operated at a lower temperature.

Compared to a process in which both reactors are operated according to the conventional two-stage process, the process of the invention has the following advantages: Higher conversions of olefins into hydroformylation products are achieved or at a constant conversion it is possible for the reaction temperature to be reduced in at least one reactor, as a result of which the selectivity to the formation of hydroformylation products is increased.

The process of the invention can be carried out in a plant having two or more hydroformylation stages using unmodified cobalt carbonyl catalysts. There are always two stages in which the first hydroformylation reactor is operated at a relatively low temperature and the second hydroformylation reactor is operated at the higher temperature. The stage in which the reaction is carried out at the higher temperature above 160° C. is operated by the one-pot process with simultaneous catalyst formation, catalyst extraction and hydroformylation. It is also possible for both hydroformylation stages which use unmodified cobalt carbonyl catalysts to be operated by the one-pot process. In the case of processes having more than two hydroformylation stages, the catalyst and the method of operation can be chosen freely for each further stage.

The process of the invention can be carried out in a number of variants. In the interests of clarity, only two-stage processes will be described.

Figure 1:
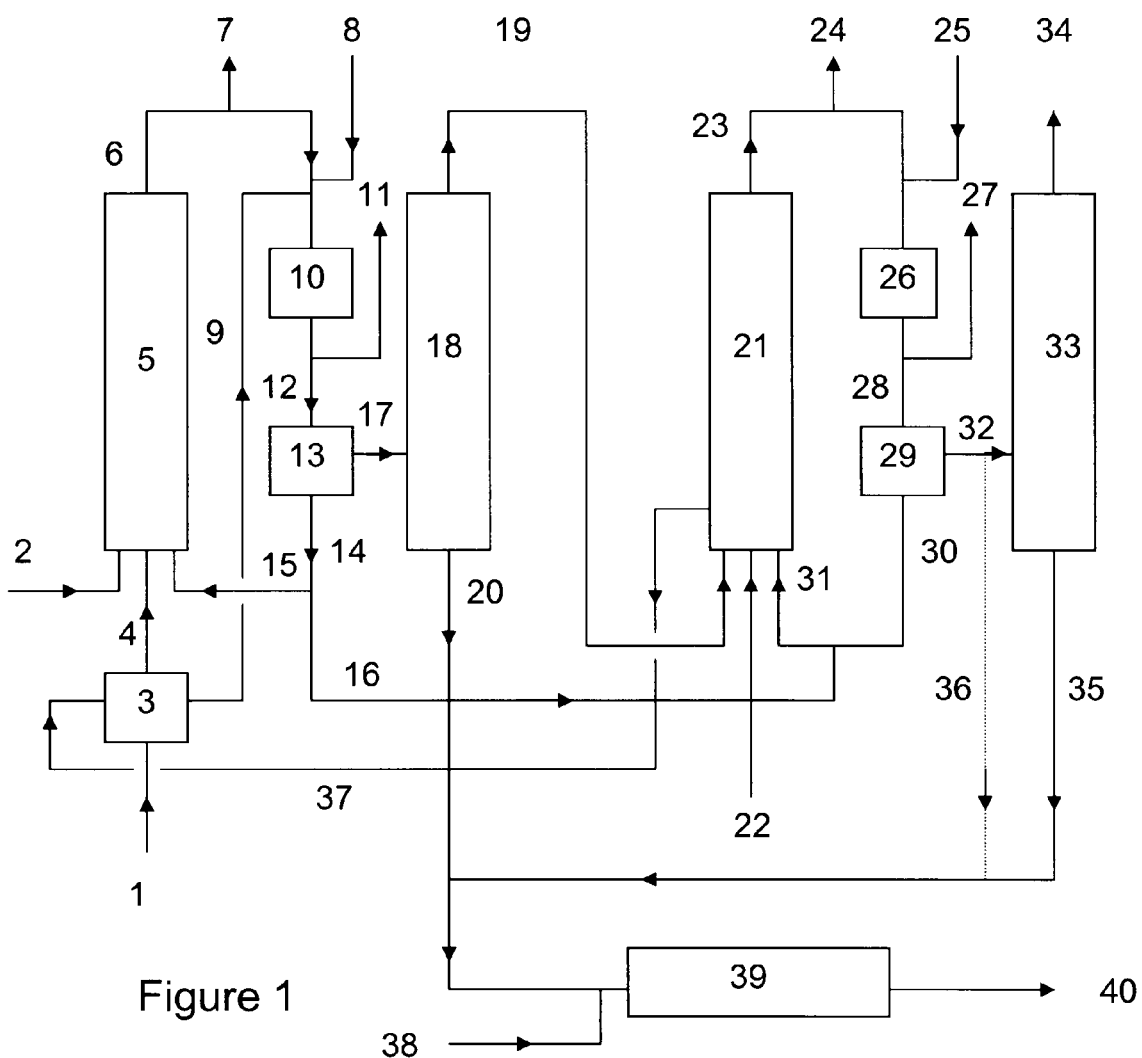
FIG. 1 and FIG. 2 are block flow diagrams describing two different variants of the process of the invention.

One variant of the process of the invention is shown as a block flow diagram in FIG. 1. The starting olefin (1) extracts cobalt carbonyls from stream (37) in the extractor (3). The extract (4), the synthesis gas (2) (carbon monoxide and hydrogen) and an aqueous cobalt salt solution (15) are fed into the hydroformylation reactor (5) which is operated at relatively low temperature. The hydroformylation mixture (6) obtained in this way is partially depressurised, the depressurisation gas (7) (unreacted synthesis gas) is taken off. The cobalt carbonyls present in the depressurised hydroformylation mixture and in the aqueous stream (9) are oxidized to cobalt salts by means of an oxygen-containing gas (8) in the cobalt removal unit (10). After the offgas (11) has been taken off, the hydroformylation mixture (12) is separated in the vessel (13) into a virtually cobalt-free organic phase (17) and an aqueous cobalt salt solution (14). A part (15) of the stream (14) is recirculated to the hydroformylation reactor (5). The other part (16) is fed into the second hydroformylation reactor (21) which is operated at the higher temperature. The catalyst-free hydroformylation mixture (17) is separated in the distillation column (18) into the low boiling fractions (19), which comprise predominantly unreacted olefins, and crude aldehyde (20). The low boiling fractions (19), synthesis gas (22) and cobalt salt solution (31) which is obtained by combining stream (16) with stream (30) are fed into the second hydroformylation reactor (21). From the reactor (21), a part (37) of the aqueous bottom phase is fed into the extractor (3) so that its level remains constant. The hydroformylation mixture (23) is partially depressurised and the depressurisation gas (24) (unreacted synthesis gas) is taken off. The cobalt carbonyls present in the depressurised hydroformylation mixture (23) are oxidized to cobalt salts by means of oxygen-containing gas (25) in the cobalt removal unit (26). After the offgas (27) has been taken off, the hydroformylation mixture (28) is separated in the vessel (29) into a virtually cobalt-free organic phase (32) and an aqueous cobalt salt solution (30) which is recirculated to the reactor (21). The catalyst-free hydroformylation mixture (32) can be separated in the column (33) into the low boiling fractions (34), which comprise predominantly saturated hydrocarbons, and crude aldehyde (35). If desired, part of the low boiling fractions (34) can be recirculated to the reactor (21) (line not shown in FIG. 1). A further embodiment of this process variant comprises feeding the catalyst-free hydroformylation mixture (32) without distillation in the column (33) (via line 36) together with the crude aldehyde (20) to the hydrogenation reactor (39). The crude aldehydes (20) and (35) or (20) and (32) are hydrogenated by means of hydrogen (38) in the hydrogenation reactor (39) to give the crude alcohols (40) which can optionally be worked up to give pure alcohol in a distillation which is not shown. If the aldehyde is the actual target product, the hydrogenation unit (39) is bypassed and, if desired, the crude aldehyde ((20) and (35) or (20) and (32)) is worked up in a distillation which is not shown.

As an alternative, each aldehyde stream can be separately worked up to give aldehydes or hydrogenated to give alcohols.

The extraction of the stream (37) in the extractor (3) can optionally be carried out using only part of the starting olefin (1).

A specific embodiment of variant 1 comprises operating the hydroformylation in the reactor (5) virtually without water by feeding no aqueous cobalt salt solution (15) into the reactor (5).

Figure 2:
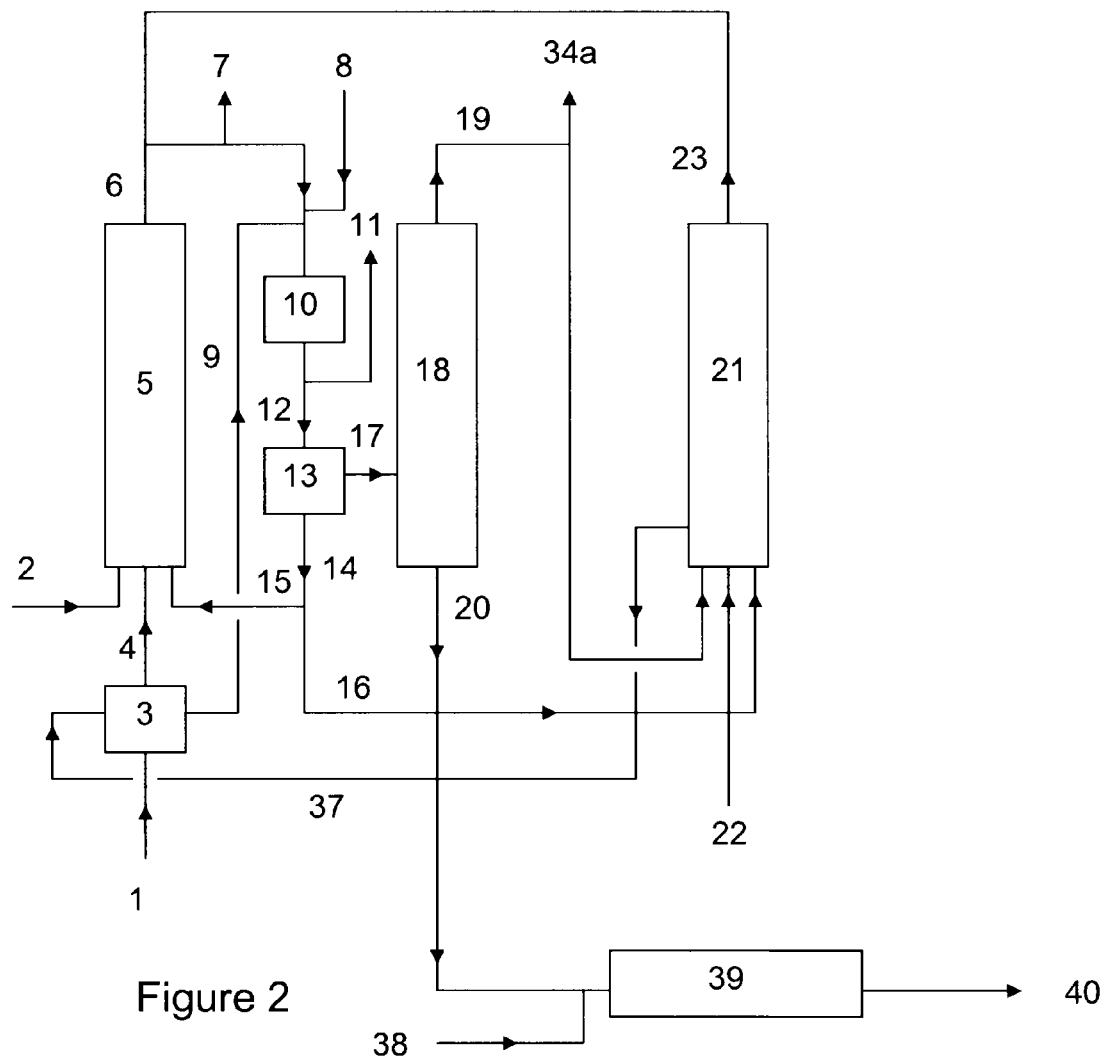

The block flow diagram of a second variant of the invention is shown in FIG. 2. The starting olefin (1) extracts cobalt carbonyls from stream (37) in the extractor (3). The extract (4), the synthesis gas (2) (carbon monoxide and hydrogen) and an aqueous cobalt salt solution (15) are fed into the hydroformylation reactor (5). The hydroformylation mixture (6) obtained in this way is partially depressurised together with the hydroformylation mixture (23) from the second hydroformylation reactor (21), the depressurisation gas (7) (unreacted synthesis gas) is taken off. The cobalt carbonyls present in the depressurised hydroformylation mixture and the aqueous stream (9) are oxidized to cobalt salts by means of an oxygen-containing gas (8) in the cobalt removal unit (10). After the offgas (11) has been taken off, the hydroformylation mixture (12) is separated in the vessel (13) into a virtually cobalt-free organic phase (17) and an aqueous cobalt salt solution (14). A part (15) of the stream (14) is recirculated to the hydroformylation reactor (5). The other part (16) is fed into the second hydroformylation reactor (21). The catalyst-free hydroformylation mixture (17) is separated in the distillation column (18) into a low boiling fraction (19), which contains the unreacted olefins and inert paraffins, and crude aldehyde (20). The low boiling fractions (19) are, after discharge of a substream (34*a*) to remove saturated hydrocarbons (paraffins) and other, nonolefinic compounds, introduced together with synthesis gas (22) and aqueous cobalt salt solution (16) into the second hydroformylation reactor (21). The hydroformylation product (23) formed is, as described above, worked up together with the first hydroformylation product (6). From the reactor (21), a part (37) of the aqueous bottom phase is fed to the extractor (3) so as to keep its level constant. The crude aldehyde (20) can be hydrogenated by means of hydrogen (38) to form the crude alcohol (40) in the hydrogenation unit (39). This alcohol can once again be worked up to give pure alcohol in a distillation which is not shown. If an aldehyde (mixture) is the target product, the hydrogenation unit is bypassed and the crude aldehyde (20) is worked up to give pure aldehyde in a distillation which is not shown.

In variant 2, the streams (6) and (23) can optionally be partially depressurised separately. It is likewise possible to oxidize the cobalt carbonyls in the streams (6) and (23) separately and separate the oxidized streams together in the vessel (13).

The discharge of the saturated hydrocarbons can also be effected by work-up of a substream of the hydroformylation product (17) which has been freed of catalyst (not shown) instead of by means of stream (34*a*). In engineering terms, this can be achieved, for example, by distillation of this substream to separate it into low boiling fractions which are discharged and an aldehyde fraction which is fed into the column (18) or combined with the crude aldehyde (20).

In variant 2, too, the hydroformylation in the reactor (5) can be carried out virtually without water by not feeding any aqueous cobalt salt solution (15) into the reactor (5).

In both variants, aqueous cobalt salt solutions can be recirculated from the separation vessel (13) and/or (29) to the upstream cobalt removal unit (10) and/or (26) (not shown in the figures).

Both in variant 1 and in variant 2, the extraction of the cobalt carbonyls from stream (37) can be carried out in the hydroformylation reactor (5) which is operated at a lower temperature than reactor (21) (not shown in the figures). This means that the aqueous phase (37) taken off from reactor (21) is introduced directly into reactor (5). Introduction of the cobalt water (15) can be omitted here. The amount of water introduced into the reactor (5) with the aqueous phase (37) can be less than, equal to or more than that which can be discharged with the hydroformylation mixture (6). In the latter case (not shown in the figures), aqueous phase is taken off to keep the level of the aqueous phase in the reactor (5) constant and introduced into the cobalt removal unit (10). Extraction of the cobalt carbonyls from stream (37) in the reactor (5) is particularly advantageous when reactor (5) is operated at such low temperatures that barely any cobalt carbonyls are formed from cobalt(II) salts under hydroformylation conditions.

In both variants, water and small amounts of cobalt compounds are discharged from the process with the products. These missing amounts can be replaced periodically or continuously. For example, an aqueous cobalt salt solution having the required concentration can be fed in at one or more places. It can also be advantageous to use cobalt salt solutions having differing concentrations. To compensate for losses, water and cobalt compounds are preferably introduced separately or as a solution into the vessel (13) and/or (29).

The common feature of the invention in variants 1 and 2 is that cobalt carbonyls are brought from the reactor which is operated at a relatively high temperature into the reactor in which the hydroformylation is carried out at a lower temperature.

In the present invention, the amount of water phase introduced with the aqueous cobalt salt solution into the reactor which is operated at a relatively high temperature is greater than that carried from the reactor with the liquid reaction mixture and the excess synthesis gas together. The relative amount of water which is discharged from the reactor operated at a relatively high temperature is dependent, in particular, on the solubility in the starting olefin (mixture) and its reaction products. In the limiting case when the hydroformylation mixture has virtually no solvent capability for water, the entire amount of water introduced with the cobalt salt solution is discharged from the reactor in order to keep the level of the aqueous phase in the reactor constant.

If di-n-butene is hydroformylated, aqueous cobalt salt solution is fed into the reactor which is operated at a relatively high temperature in such an amount that preferably from 30 to 90%, particularly preferably from 40 to 60%, of the water phase fed in has to be taken off to keep the aqueous bottom phase constant.

The reaction temperature in this reactor is in the range from 160 to 220° C., in particular in the range from 175 to 195° C.

The aqueous bottom phase which has been taken off is extracted by means of an olefin or olefin mixture which is reacted in the reactor which is operated at a lower temperature. Here, part of the cobalt carbonyls present in the aqueous phase goes over into the olefin phase.

For the extraction of the cobalt carbonyls outside a hydroformylation reactor, it is possible to use the extraction apparatuses known to those skilled in the art, for example simple extraction columns, sieve tray columns, packed columns or columns having moving internals. Examples of extraction apparatuses having moving internals are, inter alia, the rotating disc contactor and Scheibel column. A further apparatus is the mixer-settler extractor. It is also possible to combine two or more extractors of the same type or different type with one another.

In the extraction, the olefin (mixture) is preferably the disperse phase. The extraction can be carried out at the same temperature as in an upstream or downstream hydroformylation reactor or at lower temperatures. The pressures at which the extraction is carried out can correspond to those in a hydroformylation reactor. The extraction can also be carried out at a lower pressure.

The other reactor of the process of the invention is operated in the temperature range from 120 to 180° C., in particular in the range from 150 to 175° C.

The hydroformylation in each of the two stages is carried out in a high-pressure reactor, preferably a bubble column reactor. Each hydroformylation stage according to the one-pot process is preferably carried out in a cascaded bubble column reactor into which olefins, aqueous cobalt salt solution and synthesis gas are preferably introduced by means of a mixing nozzle.

The level of the aqueous bottom phase in the hydroformylation reactor(s) is kept constant or virtually constant. This means that during steady-state operation (constant reaction conditions) the phase boundary between the lower aqueous phase in which part of the organic phase is dispersed is established at a level whose height preferably fluctuates by less than ±5% about a mean. This mean height of the phase boundary can be above or below or at the height of the outlet opening of the mixing nozzle through which the starting materials are introduced into the reactor. The phase boundary can be located from 0 to 1 m, preferably from 0 to 0.5 m and particularly preferably from 0 to 0.2 m, above or below the outlet opening of the mixing nozzle.

The height of the aqueous phase can alter within the limits of the abovementioned range during a change in load. Furthermore, the height of the aqueous phase can alter within these limits as a function of throughput.

Part of the aqueous bottom phase is discharged periodically or preferably continuously from the reactor which is operated at a relatively high temperature.

In the process of the invention, aqueous solutions of cobalt salts are fed into the hydroformylation reactors. Preference is given to using aqueous solutions of cobalt salts of carboxylic acids, for example cobalt formate or cobalt acetate. It is also possible to use solutions which contain more than one cobalt compound. A particularly preferred cobalt solution is that which is, in a particularly preferred embodiment of the overall process, obtained in the oxidative removal of cobalt from the hydroformylation output. This solution, which also contains formic acid, can be used directly or after concentration or after reduction of the formic acid content, for example as described in DE 100 09 207.

Solutions whose cobalt salt concentration is greater than 30%, in particular greater than 60%, very particularly preferably greater than 80%, of the saturation limit of the cobalt salt are preferably used in the process of the invention. If mainly cobalt formate is present in the aqueous solution, the content of cobalt salts, calculated as elemental cobalt, is preferably in the range from 0.7 to 1.7% by mass.

The hydroformylation in the two reactors is preferably carried out in a manner similar to that described in DE 196 54 340 and DE 101 35 906, except that part of the bottom phase containing aqueous cobalt compounds is separated off from one reactor.

The reaction pressure is in the range from 100 to 400 bar, in particular in the range from 150 to 300 bar. The volume ratio of hydrogen to carbon monoxide in the synthesis gas used is in the range from 1:2 to 2:1.

According to the present invention, the olefin (mixture), the aqueous solution containing the cobalt compounds and synthesis gas (mixture of hydrogen and carbon monoxide) and, if appropriate, a solvent are introduced into the bottom of at least one hydroformylation reactor. The bottom of the reactor which is operated at temperatures above 160° C. to produce the active catalyst contains an aqueous phase in which small amounts of organic phase are dispersed. The aqueous phase makes up from 5 to 30%, in particular from 10 to 30%, of the liquid present in the reactor. In the other reactor, into which active cobalt catalyst is introduced, the aqueous bottom phase makes up from 0 to 20%, in particular from 5 to 15%, of the liquid present in the reactor.

To obtain a high reaction rate, it is advantageous to mix the aqueous bottom phase with the organic phase and synthesis gas and also the aqueous phase. The intensive mixing avoids concentration gradients of the reactants. Furthermore, mixing of the aqueous bottom phase with the organic phase promotes transfer of the catalyst formed into the organic phase in which the hydroformylation mainly proceeds.

The mixing of the reaction components (olefin, synthesis gas, aqueous cobalt salt solution) with themselves and/or hydroformylation mixture and also the mixing of the two liquid phases in the reactor can be effected by means of suitable engineering devices.

Olefin, synthesis gas and aqueous cobalt salt solution can be introduced separately, advantageously by means of nozzles, into the reactor. It is also possible for two components to be introduced together through one or more mixing nozzles into the reactor and the third component to be introduced separately. However, it is advantageous to feed all three components together through one or more mixing nozzles into the reactor.

The aqueous bottom phase can be circulated by means of a pump which is installed in a circulation line. Mixing of the aqueous phase and mixing of the aqueous phase with the organic phase and synthesis gas can also be achieved by feeding part of the aqueous phase from the reactor to the mixing nozzle for the reactants. This can be achieved by means of a pump.

The ejector action of mixing nozzles is influenced by the momentum of the exiting gas and the exiting liquid. High liquid velocities of from 3 to 300 m/s, particularly preferably from 10 to 100 m/s, very particularly preferably from 15 to 70 m/s, at the point or points of mixing are preferred.

The reaction mixture from a hydroformylation reactor contains starting material (olefins), products (aldehydes, alcohols, formic esters), by-products and cobalt carbonyl compounds. The latter can be separated off from the reaction mixture by means of technical measures known per se. The removal of the cobalt carbonyls is preferably carried out oxidatively. For this purpose, the reaction mixture is partially depressurised, in particular to from 10 to 15 bar, and reacted with oxygen-containing gases, in particular air or oxygen, at temperatures of from 90° C. to 160° C. in the presence of an acidic cobalt(II) salt solution in a reactor (cobalt removal unit) and in this way oxidatively freed of cobalt carbonyl compounds. These are decomposed to form cobalt(II) salts. Cobalt removal methods are well known and are comprehensively described in the literature, e.g. in "New Syntheses with Carbon Monoxide", Springer Verlag (1980), Berlin, Heidelberg, New York, page 158 ff. After oxidation, the mixture is separated into the organic product phase, offgas and process water. The process water separated off has a pH of from 1.5 to 4.5 and a cobalt content of from 0.5 to 2% by mass. The major part of the process water is recirculated to the cobalt removal unit, if appropriate with addition of water. The other part is preferably recirculated to the hydroformylation reactor.

The organic reaction mixtures obtained after removal of the cobalt carbonyls are worked up by known methods. For example, they can be separated by distillation into hydrocarbon fractions (which may contain unreacted olefins), aldehydes, other products of value (alcohols and their formates) and further substances. The hydrocarbon fractions containing unreacted olefins can be partly recirculated to the same hydroformylation according to the invention or to a further hydroformylation which can also be operated according to the invention. The aldehydes obtained can be utilised as such or can be used as starting material for the preparation of other materials, for example carboxylic acids, amines, nitriles or aldol condensation products.

Furthermore, the hydroformylation mixtures can be hydrogenated before or after removal of the unreacted olefins to form the corresponding primary alcohols which can be used, inter alia, as precursors for plasticisers or detergents.

As starting materials for the process of the invention, it is in principle possible to use all olefins having at least 5 carbon atoms. The starting materials used can be linear or branched α-olefins, linear or branched olefins having internal double bonds, cycloaliphatic olefins or olefins having aromatic groups. It is possible to use materials having one or more olefinic double bond(s). Preference is given to using olefins or olefin mixtures having from 6 to 24 carbon atoms. The mixtures can comprise olefins having the same number of carbon atoms, similar numbers of carbon atoms or significantly different numbers of carbon atoms. As olefins which can be used as starting material either in pure form, in an isomer mixture or in a mixture with further olefins having a different number of carbon atoms, mention may be made by way of example of: 1-, 2- or 3-hexene, 1-heptene, linear heptenes having an internal double bond (2-heptene, 3-heptene, etc.), mixtures of linear heptenes, 2- or 3-methyl-1-hexene, 1-octene, linear octenes having an internal double bond, mixtures of linear octenes, 2- or 3-methylheptene, 1-nonene, linear nonenes having an internal double bond, mixtures of linear nonenes, 2-, 3- or 4-methyloctenes, 1-, 2-, 3-, 4- or 5-de-cene, 2-ethyl-1-octene, 1-dodecene, linear dodecenes having an internal double bond, mixtures of linear dodecenes, 1-tetradecene, linear tetradecenes having an internal double bond, mixtures of linear tetradecenes, 1-hexadecene, linear hexadecenes having an internal double bond, mixtures of linear hexadecenes. Further suitable starting materials are, inter alia, the mixture of isomeric hexenes obtained in the dimerisation of propene (dipropene), the mixture of isomeric octenes obtained in the dimerisation of butenes (dibutene), the mixture of isomeric nonenes obtained in the trimerisation of propene (tripropene), the mixture of isomeric dodecenes obtained in the tetramerisation of propene or the trimerisation of butenes (tetrapropene or tributene), the hexadecene mixture obtained in the tetramerisation of butenes (tetrabutene) and olefin mixtures prepared by cooligomerisation of olefins having different numbers of carbon atoms, if desired after separation into fractions having the same number of carbon atoms or similar numbers of carbon atoms by distillation. Furthermore, it is possible to use olefins or olefin mixtures which have been produced by the Fischer-Tropsch synthesis. Olefins which have been prepared by olefin metathesis or by other industrial processes can also be used. Preferred starting materials are mixtures of isomeric octenes, nonenes, dodecenes or hexadecenes, i.e. oligomers of lower olefins such as n-butenes, isobutene or propene. Further well-suited starting materials are oligomers of $C_5$ olefins.

When $C_8$-, $C_{12}$- or $C_{16}$-olefin mixtures are the starting materials, particular preference is given to using ones which have been prepared by oligomerisation of linear butenes over fixed-bed nickel catalysts, for example by the Octol process (Hydrocarbon Process, Int. Ed. (1986) 65 (2. Sect. 1) pages 31-33).

The hydroformylation mixtures can be used for preparing aldehydes. The corresponding alcohols, which are used, for example, as precursors for plasticisers, detergents or lubricants, can be prepared from the hydroformylation mixtures. The corresponding carboxylic acids, which are used, for example, as precursors for surface coating additives or vinyl esters, can be prepared from the hydroformylation mixtures by oxidation.

The following examples illustrate the invention without restricting it thereto.

EXAMPLE 1

Preparation of Active Cobalt Catalyst by Precarbonylation

1a) Carbonylation at 190° C.

1000 ml of aqueous cobalt acetate solution containing 1.2% by mass of cobalt calculated as metal were placed in a 2 l stainless steel stirring autoclave. While stirring vigorously (1000 rpm), synthesis gas having a $CO/H_2$ volume ratio of 1:1 was introduced into the high-pressure autoclave at 190° C. and 280 bar. Sampling of the autoclave contents at intervals enabled the formation of the cobalt carbonyl complexes to be followed analytically during the carbonylation. After a carbonylation time of 4 hours, about 66% of the cobalt salt used had been converted into the active cobalt catalyst.

1b) Experiment 1a) was repeated using an aqueous cobalt acetate/isononanol mixture (200 ml of isononanol and 800 ml of water containing 1.2% by mass of cobalt, calculated as metal and based on the total solution) in place of the aqueous cobalt acetate solution. After only 5 minutes at 190° C., 65% of the cobalt used had been converted into cobalt carbonyl complexes.

1c) Carbonylation at 160° C.

In a third experiment, the influence of temperature on the formation of the active cobalt catalyst was examined. Here, the procedure of experiment 1a) was repeated with the sole difference that the reaction temperature was 160° C. After a carbonylation time of 4 hours at 160° C., only about 25% of the cobalt salt used had been converted into the active cobalt catalyst.

1d)

Repetition of Experiment 1c) using the same starting material mixture as in Experiment 1b resulted in 25% of the cobalt salt used having been converted into the cobalt carbonyl complexes after a time of about 50 minutes.

Comparison of Experiments 1a and 1c and of Experiments 1b and 1d shows the substantial temperature effect. Even when isononanol is added, the formation of the cobalt carbonyls at 160° C. is too slow for an industrial process.

EXAMPLE 2

Comparative Example

Nonanols by Two-Stage Hydroformylation of Dibutene

1st Stage

In a 5 l high-pressure autoclave provided with a stirrer and electric heating, 2000 g of dibutene (15.2% by mass of n-octenes, 61.9% by mass of 3-methylheptenes, 22.9% by mass of 3,4-dimethylhexenes) were hydroformylated in the presence of a cobalt catalyst at 180° C. and a synthesis gas pressure of 280 bar for 2 hours. The active cobalt catalyst had been prepared as described in Example 1a by treating 640 g of an aqueous cobalt acetate solution containing 1.2% by mass of cobalt with synthesis gas at 190° C. and 280 bar for 4 hours. After cooling and depressurisation, the cobalt carbonyls formed were transferred into the organic phase by extraction with the 2000 g of dibutene. The concentration of the active catalyst in the dibutene was 0.040% by mass based on dibutene and calculated as cobalt metal.

After cooling to 80° C. and depressurisation, the hydroformylation mixture was freed of cobalt by treatment with 5% strength by mass aqueous acetic acid in the presence of air. The cobalt-free hydroformylation mixture was subsequently separated off from the aqueous phase.

The hydroformylation was repeated five times under identical conditions. The cobalt-free hydroformylation mixtures were combined. 11 950 g of hydroformylation mixture were obtained. The composition of the product mixture according to GC analysis is shown in Table 1, column 2. According to this, the dibutene conversion was 82.7% and the selectivity to desired products was 89.6%, corresponding to a desired product yield of 74.1%. Here, nonanals, nonanols and their formates were regarded as desired products.

2nd Stage 10 500 g of cobalt-free hydroformylation mixture from the first stage were distilled in a column to recover unreacted olefins. The $C_8$-hydrocarbons (olefins and paraffins) were taken off as low boiling fractions at the top of the column, while the bottoms from the column contained the desired products and the high boiling fractions.

2000 g of the recovered $C_8$-hydrocarbon mixture comprising about 75.1% of $C_8$-olefins and about 24.9% of paraffins were hydroformylated at 185° C. and a synthesis gas pressure of 280 bar in the 5 l autoclave for 3 hours. The active cobalt catalyst was prepared as in the 1st stage and transferred into the olefin phase; its concentration was 0.040% by mass of cobalt based on the olefin and calculated as cobalt metal.

The hydroformylation mixture was cooled to 80° C., depressurised and subjected to cobalt removal as described in the 1st stage. This gave 2366 g of cobalt-free hydroformylation mixture whose composition according to GC analysis is shown in Table 1, column 3. The olefin conversion was 91% and the selectivity to desired products was 83.8%, corresponding to a desired product yield of 76.3%.

The total olefin conversion over the two stages was 98.4% at a selectivity to desired products of 88.6%, corresponding to a total desired product yield of 87.3% based on dibutene used.

EXAMPLE 3

Nonanols by Two-Stage Hydroformylation of Dibutene (according to the invention)

1st Stage

In the 5 l high-pressure autoclave used in Example 1, 2000 g of dibutene were hydroformylated at 165° C. and a synthesis gas pressure of 280 bar in the presence of an active cobalt catalyst for 4 hours. The active cobalt catalyst had been prepared and extracted into dibutene as in Example 2. The concentration of the catalyst in the dibutene was 0.040% by mass, based on dibutene and calculated as cobalt metal.

After cooling to 80° C., the hydroformylation mixture was depressurised and freed of cobalt by treatment with 5% strength by mass aqueous acetic acid and air.

The hydroformylation was repeated five times under identical conditions.

The cobalt-free hydroformylation mixtures were combined. 11 750 g of hydroformylation mixture were obtained; the composition according to GC analysis is shown in Table 2, column 2. According to this, the dibutene conversion was 72.4% and the selectivity to desired products was 94.2%, corresponding to a desired product yield of 68.2%. Here, nonanals, nonanols and their formates were regarded as desired products.

It can be seen that the selectivity to desired products in the hydroformylation at 165° C. was significantly higher than in the hydroformylation at 180° C., as in the first stage of Example 2.

2nd Stage 10 000 g of cobalt-free hydroformylation mixture from the first stage were distilled in a column as in Example 2 for the purpose of recovering the unreacted olefins. The $C_8$-olefins and $C_8$-paraffins were taken off as overhead fraction, while the bottoms from the column contained the desired products and the high boiling fractions. 2000 g of recovered $C_8$-hydrocarbon mixture (95.1% of $C_8$-olefins and 4.9% of paraffins) were hydroformylated at 185° C. and a synthesis gas pressure of 280 bar in the 5 l autoclave of the first stage for 5 hours. The cobalt catalyst had been prepared and transferred into the olefin phase as in Example 2; its concentration was 0.045% by mass based on the olefin and calculated as cobalt metal.

The hydroformylation mixture was cooled to 80° C., depressurised and freed of cobalt, as described in the 1st stage. This gave 2465 g of cobalt-free hydroformylation mixture whose composition according to GC analysis is shown in Table 2, column 3. The olefin conversion was 91.8% and the selectivity to desired products was 84.8%, corresponding to a desired product yield of 77.9%.

The total olefin conversion over the two stages was 97.7% at a selectivity to desired products of 91.8%, corresponding to a total desired product yield of 89.7% based on dibutene used.

TABLE 1

Composition of cobalt-free hydroformylation product mixtures Example 2

|  | Ex. 2, 1st stage % by mass | Ex. 2, 2nd stage % by mass |
| --- | --- | --- |
| $C_8$-Olefins | 14.5 | 5.7 |
| $C_8$-Paraffins | 4.8 | 24.5 |
| $C_9$-Aldehydes | 58.8 | 38.3 |
| Nonyl formates | 3.5 | 4.8 |
| $C_9$-Alcohols | 17.1 | 19.4 |
| High boiling fractions | 1.3 | 7.3 |

TABLE 2

Composition of cobalt-free hydroformylation product mixtures Example 3

|  | Ex. 3, 1st stage % by mass | Ex. 3, 2nd stage % by mass |
| --- | --- | --- |
| $C_8$-Olefins | 23.5 | 6.3 |
| $C_8$-Paraffins | 1.2 | 8.6 |
| $C_9$-Aldehydes | 59.8 | 43.0 |
| Nonyl formates | 3.2 | 5.6 |
| $C_9$-Alcohols | 11.3 | 29.0 |
| High boiling fractions | 1.0 | 7.5 |

The process of the invention thus gives, as comparison of Example 3 with Example 2 shows, a 2.4% higher product yield.

The invention claimed is:

1. A process for the continuous preparation of an aldehyde and/or alcohol having at least 6 carbon atoms by multistage hydroformylation of an olefin or olefin mixture having at least 5 carbon atoms in the presence of unmodified cobalt complexes, in which at least two reactors are operated at different temperatures in the temperature range from 100 to 220° C. and pressures of from 100 to 400 bar, wherein
   a) one reactor is operated at temperatures above 160° C. by the one-pot process with simultaneous catalyst formation, catalyst extraction and hydroformylation and the amount of water fed into the reactor with the aqueous cobalt salt solution is greater than that discharged from the reactor with the liquid reaction mixture and the gas phase together, with part of the aqueous bottom phase being discharged from the reactor to keep the level of the aqueous bottom phase constant, and
   b) the cobalt carbonyls in the aqueous phase taken off or part thereof are introduced into the reactor which is operated at a lower temperature.

2. The process according to claim 1, wherein cobalt carbonyls in the aqueous phase taken off are extracted by means of an olefin or olefin mixture and the olefin extract containing cobalt carbonyls is fed into the reactor which is operated at a relatively low temperature using unmodified cobalt catalysts.

3. The process according to claim 1, wherein the aqueous phase taken off is introduced into the reactor which is operated at a relatively low temperature using unmodified cobalt catalysts.

4. The process according to claim 1, wherein the hydroformylation is carried out in two stages.

5. The process according to claim 4, wherein the reaction temperature in the reactor which is operated at a relatively high temperature is in the range from 160 to 220° C. and the reaction temperature in the reactor which is operated at a lower temperature is in the range from 120 to 180° C.

6. The process according to claim 4, wherein the reaction temperature in the reactor which is operated at a relatively high temperature is in the range from 175 to 195° C. and the reaction temperature in the reactor which is operated at a lower temperature is in the range from 150 to 175° C.

7. The process according to claim 1, wherein an olefin or olefin mixture having from 6 to 24 carbon atoms is hydroformylated.

8. The process according to claim 7, wherein an olefin or olefin mixture having from 8 to 16 carbon atoms is hydroformylated.

9. The process according to claim 7, wherein a butane oligomer is hydroformylated.

10. Process according to claim 9, wherein an oligomer prepared from linear butenes using fixed-bed nickel catalysts is hydroformylated.

* * * * *